United States Patent [19]

Deutsch

[11] Patent Number: 5,028,526
[45] Date of Patent: Jul. 2, 1991

[54] METHOD FOR SEMEN ANALYSIS

[75] Inventor: Alice Deutsch, 889 Broadway, New York, N.Y. 10003

[73] Assignee: Alice Deutsch, New York, N.Y.

[21] Appl. No.: 339,505

[22] Filed: Apr. 17, 1989

[51] Int. Cl.$^5$ ............................................... C12O 1/00
[52] U.S. Cl. ...................................... 435/7.21; 435/2; 435/4; 435/14; 435/21; 435/23; 435/7.2; 435/7.8; 436/63; 436/906
[58] Field of Search ...................... 435/2, 6, 7, 18, 21, 435/23, 803, 810, 7.21, 7.2, 7.8; 436/94, 165, 906

[56] References Cited

U.S. PATENT DOCUMENTS

| | | | |
|---|---|---|---|
| 3,909,363 | 9/1975 | Bucalo | 436/906 |
| 4,009,260 | 2/1977 | Ericsson | 435/2 |
| 4,225,405 | 9/1980 | Lawson | 435/2 |
| 4,356,259 | 10/1982 | Banba | 435/2 |
| 4,767,703 | 8/1988 | Ax et al. | 436/906 |

OTHER PUBLICATIONS

Millititer TM Filtration System; Millipore Corporation, Bedford, Ma. (1984).
Schill; Woff; International Journal of Fertility 19(4) pp. 217-223, (1974).
Harel; Nelken; American Journal of Reproductive Immunology and Microbiology 8 (4) pp. 137-140 (1985).
Fritz et al; Chemical Abstracts CA 78 (3):13207h (1972).
Messineo et al; Chemical Abstracts CA 78 (23):144897f (1982).
Millipore Catalog, (Nov. 1986).
Pall BioSupport Product Information (Undated).

*Primary Examiner*—Sam Rosen
*Attorney, Agent, or Firm*—Hedman, Gibson, Costigan & Hoare

[57] ABSTRACT

A method is disclosed for the separation of seminal plasma from semen by means of a membrane. The invention also includes a method for the determination of enzymes such as acrosin and other components of semen.

9 Claims, No Drawings

METHOD FOR SEMEN ANALYSIS

BACKGROUND OF THE INVENTION

Semen consists of a mixture of particulates including spermatozoa, other cells and a liquid portion, which comprises proteins, hormones and other dissolved or suspended molecules collectively known as seminal plasma. Seminal analysis and evaluation is a routine diagnostic procedure that is carried out in connection with fertility studies. Specimens should be analyzed within two hours of collection which places a time constraint on the analytical technique.

The analysis of semen involves the separation of the solid content from the liquid material. This has been done in the prior art by mechanical centrifugation using conventional techniques and an applied force of 500 to 1000 g for 10 to 30 minutes. The difficulty in separating the contents of semen using this type of a procedure is that the separated seminal plasma must be manually withdrawn from the centrifuge container before removal of the pellet which contains the separated spermatozoa. The pellet requires further washing to remove traces of the seminal plasma and resuspension in a suitable liquid. Analyses which require the separation of spermatozoa from seminal plasma include the determination of acrosin (Mohsenian et al., 1982 Fertil. Steril., 37:223-229; Goodpasture et al., J. Reprod. Fertil., 1981, 63:397-405; Goodpasture et al., J. Androl. 1982, 3:151-156; Goodpasture et al., J. Androl. 1987, 8:267-271; Schill. Fertil. Steril. 1975, 26:711-720; Schill et al., Int. J. Fertil. 1974, 19:217-227; Zaneveld et al., J. Reprod. Fertil. 1973, 32:525-529, all of which are incorporated by reference); hyaluronidase; acid phosphatases; $\beta$-galactosidase; $\beta$-N-acetylgalactosaminidase; $\beta$-galactosidase (Mack et al. 1983, Biol. Reprod., 28:1032-1042) and anti-sperm antibodies (WHO Laboratory Manual for the Examination of Human Semen and Semen-Cervical Mucous Interaction, 1987, Cambridge Univ. Press NY, N.Y., which is incorporated by reference). Seminal plasma is usually used for the determination of zinc, citric acid, fructose (all described in WHO Laboratory Manual), hormones such as relaxin (Weiss et al. 1986, Am. J. Obstetr. Gynecol. 154: 749-755) or metabolites such as glycerophosphocholine (Chap et al. 1988, Clin. Chem. 34: 106-109).

The centrifugation which is used in the separations that are required for seminal analyses is time consuming and difficult for running multiple samples. The required sample size of about 1.0 ml makes it impossible to analyze the same semen sample that is used for in vitro fertilization or artificial insemination.

Aside from the drawbacks of centrifugation, several assays for anti-sperm antibodies also have weaknesses. These assays use 1) agglutination (reviewed in R. Bronson et al. Fertil. Steril. (1984) 42: 171-183) which is very subjective and may give false negative and false positive results, 2) microscopic examination and counting of beads on the sperm surface (Bronson et al. 1982. Arch. Androl. 9: 61) which is labor-intensive and somewhat subjective, or 3) enzyme immunoassay of immobilized sonicated sperm including both intracellular and cell-surface antigens (W. Harel and D. Nelken. 1985. Am. J. Reprod. Immunol. Microbio. 8:137) which can give false-positive and false-negative results.

SUMMARY OF THE INVENTION

The present invention is concerned with an improved method for the separation of seminal plasma from the particulates in semen. The improved method comprises separating seminal plasma from semen by means of a membrane which allows only the seminal plasma to pass and retains particulates on the membrane surface. Synthetic hydrophilic, microporus membranes are preferred because they are inert towards semen. If only the spermatozoa are going to be analyzed, then the seminal plasma is simply removed and discarded. If the seminal plasma is going to be analyzed, then the filtrate from the semen can preferably be collected into 96 individual wells of a 96 multi-well non-porous plate using a collector such as the transfer guide available from Millipore or by positioning the plate immediately beneath the membrane plate and then applying a vacuum. The invention also provides a novel means for the determination of acrosin and for the determination of sperm antibodies.

It could not have been predicted prior to testing semen on a polymeric membrane surface that the membrane would be unreactive with any component in semen. In addition, it could not have been predicted whether or not the polymeric membrane surface could denature any of the enzymes in semen, interfere chemically with the various semen analysis assays, destroy the cell integrity, react nonspecifically with antibodies or tie up any binding sites that would interfere with an antibody assay.

Some advantages of the present invention associated with no centrifugation are 1) faster assays, 2) easier handling of large numbers of samples, 3) inexpensive, 4) no loss of either part of the sample, and 5) miniaturization of current assay formats to reduce sample and reagent volumes. Furthermore, the use of a 96-well membrane plate format can take advantage of recent improvements in multi-sample handling such as multichannel pipettors and 96-well plate reader spectrophotometers, colorimeters, luminometers, and fluorimeters and their respective data reduction capabilities.

Accordingly, it is a primary object of this invention to provide a novel means for the separation of seminal plasma from particulates in semen.

It is also an object of this invention to provide a novel method for the separation of seminal plasma from particulates in semen which avoids the use of a centrifuge and the associated mechanical manipulative steps.

It is also an object of this invention to provide a rapid separation technique which may be applied to very small samples.

It is also an object of this invention to provide a separation technique that permits the determination of a plurality of components using the same sample rather than multiple samples.

It is also an object of this invention to provide a separation technique that permits the simultaneous determination of a plurality of samples rather than a small number of samples that must be processed sequentially.

It is also an object of this invention to provide a novel method for the determination of acrosin activity in spermatozoa.

It is also an object of this invention to provide a novel method for the determination of sperm antibodies.

These and other objects will become apparent from the detailed description of the invention.

DETAILED DESCRIPTION OF THE INVENTION

The separation of seminal plasma is achieved by (a) applying a semen sample to the upper surface of a membrane; and (b) collecting the seminal plasma at the lower surface of said membrane.

The process of the invention may be used in the analysis of semen from humans, domesticated animals and animals normally found in zoological collections. Generally, it is preferred to dilute the semen sample with an isotonic buffer solution such as phosphate buffer solution prior to separation. Dilutions of 1:2 to 1:50 of semen in isotonic buffer solution and more preferably from 1:10 to 1:20 may be utilized. The use of a diluent facilitates the separation of particulates from the seminal plasma. Preferably, the membrane is mounted in a multiwell membrane plate of the type disclosed in U.S. Pat. Nos. 4,427,415; 4,734,192; and 4,797,259, which are incorporated by reference. Generally, it is preferred to employ polymeric membranes having a porosity which is sufficient to retain particulates while allowing the plasma to pass through the membrane. The polymeric membrane, as opposed to an ordinary paper filter, will allow fluid to be retained in each well until vacuum pressure is applied. With an ordinary paper filter, liquid will drip through from the force of gravity alone. The failure to retain fluid would prevent the use of the well as the reaction vessel for an assay. The material which the polymer is made of is not critical, but it should be a low protein binding material. A low protein binding material is one that does not absorb a sufficient amount of a protein, i.e., albumin or an immunoglobulin which would interfere with the subsequent assay of the spermatozoa. Polycarbonates, polyamides or polyvinylidene difluoride may be utilized for making the membrane using conventional technique. A useful average pore size diameter in the membrane is about 0.15–3.0 um, but the precise pore size is not critical and may be varied depending on the degree of separation that is desired. Membranes with smaller diameter pores may tend to clog and retard flow rates and those with average pore diameter of up to about 3.0 um will exhibit higher flow rates. The thickness of the membrane is not critical and membranes having a thickness of from 1 to 50 microns may be used in combination with a conventional porous support structure.

It is preferred to apply vacuum to the membrane using the vacuum generated by a flow of water, a portable vacuum pump or an external vacuum source to facilitate the filtration step.

After the separation of the seminal plasma, the spermatozoa may be analyzed directly on the membrane without further manipulative steps. The use of a multiwell membrane plate provides discrete samples that may be subjected to direct analysis without further manipulation.

The novel acrosin assay of the invention comprises (a) the separation of the seminal plasma using a membrane and (b) the determination of acrosin activity of spermatozoa using a colorimetric method of analysis that is based on a chromogenic substance. The hydrolysis of a colorless substrate quantitatively produces a highly colored soluble product which provides a means for measuring the enzyme activity. For example, an amino acid containing substrate such as N-benzoyl-DL-arginine-p-nitroanilide hydrochloride or N-benzyl-oxycarbonyl-L-phenyl-alanyl-L-valyl-L-arginine-p-nitroanilide hydrobromide can be used. Because acrosin is not readily available, trypsin which is a different serine protease having hydrolytic activity similar to that of acrosin can be used as a positive control. For this reason, a suitable formulation of trypsin may be included in kits for the determination of acrosin.

The detection of sperm antibodies comprises (a) the separation of seminal plasma from particulates, (b) contacting the particulates with alkaline phosphatase or another appropriate enzyme such as peroxidase, glucose oxidase, or urease conjugated to an anti-immunoprotein such as an immunoglobulin or another protein such as protein A or protein G which will bind to immunoglobulin and (c) spectrophotometrically or using some other detection system such as a system which is based on fluorescence, chemiluminscence, and the like determining the amount of antibody which binds to the sperm by measurement of the antibody bound alkaline phosphatase-anti-immunoglobulin.

Alternately, after the separation of the spermatozoa, the seminal plasma which can be collected into individual wells of a 96-well plate may be analyzed directly.

The detection of fructose comprises (a) the separation of seminal plasma from particulates, (b) contacting the seminal plasma with zinc sulfate and sodium hydroxide solutions, (c) separating the solution produced in step (b) from particulates using a second membrane plate, (d) contacting the solution separated in step (c) with indol reagent and concentrated hydrochloric acid, and (e) spectrophotometrically determining the amount of fructose present in seminal plasma.

Generally, kits for semen analysis will include a membrane plate and a reagent system suitable for the determination of one or more constituents of semen. These components may be selected according to the particular test which is to be carried out. The method for the determination of acrosin activity in a semen sample can be practiced by using a kit comprising:

(a) a suitable membrane plate, such as a 96-well membrane plate;
(b) washing buffer, such as phosphate buffered saline (PBS);
(c) detergent solution, such as an ethoxylated alcohol, i.e., octyl phenoxyl polyethoxy ethanol;
(d) enzyme substrate, such as a chromogenic arginine substrate; and
(e) a reference amount of trypsin or another protease with acrosin-like activity.

The method for the determination of anti-sperm antibodies can be practiced by using a kit comprising:
(a) a 96-well membrane plate;
(b) washing buffer, such as PBS;
(c) given amounts of labeled anti-human immunogobulins A, G, and M using alkaline phosphatase or any other suitable enzyme as the label;
(d) enzyme substrate; and
(e) positive and negative serum controls.

The method for the determination of fructose in seminal fluid can be practiced by using a kit comprising:
(a) a 96-well membrane plate and a 96-well plate;
(b) given amounts of zinc sulfate, sodium hydroxide, indol reagent and concentrated hydrochloric acid; and
(c) fructose standards.

The reagent systems for many tests are known and may be selected according to the specific assay protocol.

DESCRIPTION OF THE PREFERRED EMBODIMENTS

The specific embodiments are added to illustrate the practice invention and are not intended to limit the scope of the invention.

EXAMPLE 1

A fresh human semen sample in a cup is obtained from a donor. The sample is allowed to liquefy for about 30 minutes at room temperature. An aliquot is removed for counting. The count is $27 \times 10^6$ cells per ml. A series of dilutions is made using phosphate buffered saline, pH 7.4 (PBS). The dilutions are 1:2; 1:4; 1:8; and 1:16 in PBS. One hundred microliters of each dilution is pipetted into the well of a 1.2 micron pore size 96 well membrane plate where the wells have a capacity of about 400 ul and the membrane filter area is 0.28 cm². Vacuum is applied from a water stream for about 60 seconds. There is virtually no detectable separation of the 1:2 dilution; the seminal plasma is readily separated from the other dilutions.

EXAMPLE 2

A fresh semen sample in a cup is obtained from a donor. The sample is allowed to liquefy for about 30 minutes room temperature. An aliquot is removed for counting. Cell number is determined to be $78 \times 10^6$ cells/ml. A series of semen dilutions are prepared using phosphate-buffered saline, pH 7.4 (PBS consists of 1440 mg/L $KH_2PO_4$ + 90 g/L NaCl + 7950 mg/L $Na_2HPO_4$ in water, available from Whittaker M.A. Bioproducts). One hundred ul of each dilution is pipetted into the well of a 1.2 um membrane plate from Pall Corp. (product no. SM120L). Controls are no semen, PBS alone. The plate is placed on a vacuum manifold (from Isolab).

Vacuum is applied (house vacuum) so as to remove all liquid in the wells without breaking the membrane. About 400 µl PBS is added to each well with the vacuum on. This washing method is repeated. When all the wells are completely free of liquid, the vacuum is turned off. The bottom of the wells are blotted with absorbent paper. Then 200 µl freshly prepared substrate-detergent [2.3 mM N-benzoyl-dl-arginine p-nitroanilide hydrochloride (BAPA), 10% dimethyl sulfoxide, 0.1% Triton-X 100 (octyl phenoxyl polyethoxy ethanol), 0.055 M Hepes (N-[2-hydroxyethyl]-piperazine-N'-[2-ethanesulfonic acid] and 0.055 M NaCl, pH 8.0) is added to each well. After 180 minutes incubation at room temperature, 10 µl of 500 mM benzamidine solution is added to each well. The contents of each well are removed and read in a spectrophotometer at 405 nm wavelength. The results are shown below:

| Semen Dilution | Number of Spermatozoa | Optical Density at 405 nm | Acrosin Activity* |
|---|---|---|---|
| 1:10 | $7.8 \times 10^5$ | 0.379 | 57 µIU/$10^6$ sperm |
| 1:100 | $7.8 \times 10^4$ | 0.042 | 63 µIU/$10^6$ sperm |
| 1:1000 | $7.8 \times 10^3$ | 0.000 | — |
| PBS | 0 | 0.000 | — |

*One IU of acrosin activity is defined as the amount of enzyme that hydrolyzes 1 µmol BAPA/min at 37° C. The uIU acrosin per million spermatozoa is calculated as the difference in optical density at 410 nM between the mean of the test assays and the control, multiplied by one million, and divided by [the product of 9.9 mM$^{-1}$·cm$^{-1}$ times 180 min. times the number of sperm in millions added to each tube divided by the total volume (1.2 ml)]. A change in absorbance of 9.9 corresponds to the hydrolysis of 1.0 umol of BAPA. For simplicity, the following formula can be applied:

$$\mu IU\ acrosin/10^6\ sperm = \frac{[(mean\ OD_{test}) - OD_{control}] \times 10^6}{1485 \times numbers\ of\ sperm\ (in\ million)}$$

EXAMPLE 3

The presence of sperm-reactive antibodies in test antiserum is assayed on control spermatozoa. A fresh semen sample in a cup is obtained from a donor. The sample is allowed to liquefy for about 30 minutes room temperature. An aliquot is removed for counting. The cell number is determined to be $96 \times 10^6$ cells/ml. The semen is diluted using PBS by adding 100 ul of semen to 1900 ul of PBS. Then 100 ul of the diluted semen is pipetted into the wells of a 0.22 um Durapore (product no. STGV 09610) plate from Millipore. The plate is placed on a vacuum manifold (from Isolab). Vacuum is applied so as to remove all liquid in the wells. About 400 ul PBS is added to each well with the vacuum on. This washing method is repeated. When all the wells are completely free of liquid, the vacuum is turned off. The bottom of the wells are blotted with absorbant paper. Either PBS or normal (nonreactive) or test antiserum diluted 1:20 with PBS are added to the appropriate wells. The contents of each well are incubated at room temperature 10 minutes. The well contents are washed as above. Next 20 ul of goat anti-human immunoglobulin A conjugated to alkaline phosphatase (anti-IgA-AP, purchased from Cappel) is diluted by adding 5 ul to 4 ml PBS and added to the appropriate wells. This is repeated using 20 ul of goat anti-human immunoglobulin G conjugated to alkaline phosphatase (anti-IgG-AP, purchased from Cappel) diluted by adding 5 ul to 6 ml PBS and 20 ul of goat anti-human immunoglobulin M conjugated to alkaline phosphatase (anti-IgM-AP, purchased from Cappel) diluted by adding 5 ul to 5 ml PBS. The contents of the wells are incubated for 10 minutes and then washed as above. To each well is added 200 µl freshly prepared substrate. The substrate is 5 mg paranitrophenyl phosphate dissolved in 5 ml buffer [26.2 g diethanolamine dissolved in 250 ml water, pH 9.8, with 1 ml magnesium chloride (2.03 g $MgCl_2.6H_2O$ in 20 ml water)]. After 15 minutes incubation, the contents of each well are removed and read in a spectrophotometer at 405 nm wavelength. The results are shown below:

| Sample | Optical Density | | |
|---|---|---|---|
| | anti-IgA-AP | anti-IgG-AP | anti-IgM-AP |
| sperm alone | .050 (1%)* | .056 (1%) | .023 (1%) |
| normal serum | .036 (1%) | .130 (2%) | .187 (3%) |
| positive serum 1 | .271 (9%) | .627 (19%) | .861 (23%) |
| positive serum 2 | .718 (24%) | 1.158 (51%) | .670 (22%) |

*Values in parentheses correspond to percent binding values obtained with the Immunobead Test (BioRad).

EXAMPLE 4

A fresh semen sample in a cup is obtained from a donor. The sample is allowed to liquify for about 30 min. room temperature. An aliquot is diluted 1:50 with PBS (100 ul semen+4900 ul PBS). Then 200 ul of the diluted semen is pipetted into the wells of a 1.2 um membrane plate from Pall Corp. (product no. SM120L). The plate is placed on a vacuum manifold (from Isolab). Vacuum is applied so as to remove all liquid in the wells and collect individual filtrates into a 96-multiwell plastic plate positioned immediately beneath the membrane plate. Then 60 $\mu$l of 1.8% (w/v) $ZnSO_4 \cdot 7H_2O$ are added to each well. The plate is gently shaken to mix. 40 $\mu$l of 0.1 M NaOH are added and the plate is gently shaken to mix. The plate and contents are incubated 15 min. at room temperature. The contents are transferred to a second 1.2 um membrane plate and vacuum is applied so as to remove all liquid in the wells and collect individual filtrates into a 96-multiwell plastic plate positioned immediately beneath the membrane plate. A 250 $\mu$l portion of each filtrate is transferred to glass test tubes with glass stoppers. For controls, 250 $\mu$l of each working fructose standard which are 0.28 mM and 0.14 mM fructose diluted up fresh from a frozen stored stock of 2.8 mM fructose are used with 250 $\mu$l distilled water as a reagent blank. To each glass test tube 250 ul indol reagent are added. The indol reagent is made by first dissolving 200 mg benzoic acid in 100 ml water at 60° C., then adding 25 mg indol and filtering the solution before stirring at 4° C. Then 2.5 ml concentrated HCl are added to each test tube. The test tubes are stoppered and incubated 20 min. at 50° C. They are cooled in ice water to room temperature and the O.D. is read at 470 nm.

The fructose concentration (mmol/L) in seminal plasma is calculated according to the equation:

$$[\text{fructose}] \, (mmol/L) = OD_{470} \times F \times 75$$

where F=mean fructose standard factor according to the formula:

$$F = \frac{0.14/s_1 + 0.28/s_2}{2}$$

where $s_1$ and $s_2$ are the mean optical density readings for the 0.14 mM and 0.28 mM fructose standards, respectively; 75 is the dilution factor of seminal plasma.

I claim:

1. In a method for the determination of acrosin in semen the improvement comprising applying semen to a membrane having an average pore diameter of 0.15-3.0 um which only allows the seminal plasma to pass through the membrane surface while retaining particulates on said membrane.

2. A method as defined in claim 1, wherein said membrane is mounted in a multiwell membrane plate.

3. A method as defined in claim 2, which includes a further step of carrying out an assay in at least one well of said membrane plate.

4. A method as defined in claim 1, wherein vacuum is used in the membrane separation.

5. A method for the determination of acrosin in semen said method comprising separating seminal plasma from semen by means of a membrane which only allows the seminal plasma to pass and retain particulates; and thereafter, determining the amount of acrosin which is present in said particulates.

6. A method for the determination of acrosin in semen as defined in claim 5, said method consisting essentially of diluting semen with a diluent and thereafter separating seminal plasma from said diluted semen by means of a membrane which only allows the seminal plasma to pass and retains particulates; and thereafter determining the amount of acrosin by (a) adding an acrosin detecting reagent to said sample on said membrane; (b) incubating said sample on said membrane for a period of time; and (c) reading the results in a spectrophotometer.

7. A method as defined in claim 6 wherein the diluent is an isotonic buffer solution and the dilution is from 1:2 to 1:50 of semen to isotonic buffer solution.

8. A method for the determination of acrosin in semen, said method comprising separating seminal plasma from semen by means of a membrane which only allows the seminal plasma to pass and retain particulates; contacting the particulates with a solution of N-benzolyl-DL-arginine-p-nitroanilide hydrochloride or N-benzyl-oxycarbonyl-L-phenyl-alanyl-L-valyl-L-arginine-p-nitroanilide hydrobromide and a surface active agent and determining acrosin using a spectrophotometer.

9. A method as defined in claim 8, wherein a vacuum is applied to the membrane to facilitate the separation of the seminal plasma.

* * * * *